(12) United States Patent
Dufek

(10) Patent No.: US 11,471,316 B2
(45) Date of Patent: Oct. 18, 2022

(54) LIMB RESTRAINT

(71) Applicant: David A. Dufek, Port Orange, FL (US)

(72) Inventor: David A. Dufek, Port Orange, FL (US)

(73) Assignee: David A. Dufek, Port Orange, FL (US)

( * ) Notice: Subject to any disclaimer, the term of this patent is extended or adjusted under 35 U.S.C. 154(b) by 892 days.

(21) Appl. No.: 15/905,198

(22) Filed: Feb. 26, 2018

(65) Prior Publication Data

US 2018/0325717 A1   Nov. 15, 2018

Related U.S. Application Data

(60) Provisional application No. 62/503,821, filed on May 29, 2017.

(51) Int. Cl.
*A61F 5/37* (2006.01)
*A61G 1/044* (2006.01)

(52) U.S. Cl.
CPC .......... *A61F 5/3761* (2013.01); *A61F 5/3769* (2013.01); *A61F 5/3776* (2013.01); *A61F 5/3792* (2013.01); *A61G 1/044* (2013.01)

(58) Field of Classification Search
CPC ........ A61F 5/37; A61F 5/3707; A61F 5/3715; A61F 5/3723; A61F 5/373; A61F 5/3761; A61F 5/3769; A61F 5/3776; A61F 5/3784; A61F 5/3792; A61F 15/007; A61G 1/04; A61G 1/042; A61G 1/044; A61G 7/0526; E05B 75/00; E05B 75/005; A61B 17/132; A61B 17/1322; A61B 17/135; A01K 27/00; A01K 27/003; A01K 27/004; A45C 13/30; A45C 2013/306
See application file for complete search history.

(56) References Cited

U.S. PATENT DOCUMENTS

| | | | | |
|---|---|---|---|---|
| 4,422,455 A | * | 12/1983 | Olsen | A61F 5/3761 128/878 |
| 4,699,132 A | * | 10/1987 | Carville | A61F 5/3776 128/876 |
| 5,076,288 A | * | 12/1991 | Millard | A61F 5/3776 128/869 |
| 5,581,853 A | * | 12/1996 | Miller | A61F 5/3761 24/302 |

(Continued)

OTHER PUBLICATIONS

Frangible, definition 1, The Free Dictionary, https://www.thefreedictionary.com/frangible (Year: 2020).*

(Continued)

*Primary Examiner* — Keri J Nelson
(74) *Attorney, Agent, or Firm* — Warner Norcross + Judd LLP

(57) ABSTRACT

A restraint system includes a restraint assembly and an anchor to releasably mount the restraint assembly to a component. The restraint assembly includes a tether and a cuff coupled to the tether. In addition, the restraint assembly includes a frangible cover operable to hold the tether and the cuff in a compact, stowed configuration and is sufficiently frangible to allow a person to tear open the cover. The tether is coupled to the anchor and when the cover is opened, the tether and the cuff are operable to be deployed from their stowed configuration, and the cuff extended from the anchor.

14 Claims, 16 Drawing Sheets

(56) References Cited

U.S. PATENT DOCUMENTS

| | | | | |
|---|---|---|---|---|
| 6,318,612 | B1* | 11/2001 | MacNeil | B60R 9/048 |
| | | | | 224/330 |
| 7,195,529 | B1* | 3/2007 | Crandall | B63C 9/08 |
| | | | | 441/106 |
| 2002/0092531 | A1* | 7/2002 | Chapman | E05B 75/00 |
| | | | | 128/878 |
| 2003/0066535 | A1* | 4/2003 | Chapman | A61F 5/3776 |
| | | | | 128/869 |
| 2003/0121524 | A1* | 7/2003 | Chapman | A61F 5/3776 |
| | | | | 128/869 |
| 2008/0148533 | A1* | 6/2008 | Calkin | A61G 1/044 |
| | | | | 24/302 |
| 2017/0165097 | A1* | 6/2017 | Patmore | A61G 7/0526 |

OTHER PUBLICATIONS

Break, definition 3, The Free Dictionary, https://www.thefreedictionary.com/break (Year: 2020).*

Film, definition 2, Dictionary.com, https://www.dictionary.com/browse/film (Year: 2020).*

"Polyamide Fibers (Nylon)", Polymer Properties Database, https://polymerdatabase.com/Fibers/Nylon.html (Year: 2020).*

* cited by examiner

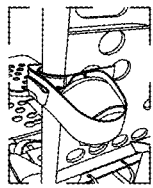
Installation of right wrist position. This position is located on the head of the stretcher, on the patients left side ← 400

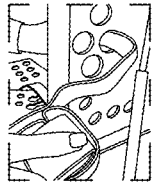
1. Place the long loop Velcro end and secondary securement strap together. Feed both the loop Velcro and secondary securement strap all the way through the second hole on left side of stretcher. ← 410

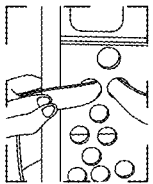
2. Bring the same loop end around frame back to the edge of the first hole. Continue to hold this position through the third step. ← 420

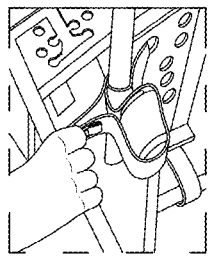
3. While holding the long looped Velcro end, tightly pull the short hook Velcro over connecting the two sides. Press firmly to join the black hook and black loop Velcro together. The black containment cover should sit flush against the stretcher frame as shown in photo. ← 430

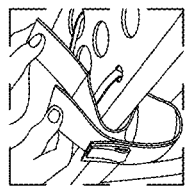
4. Once tightly secured, join the grey hook Velcro (secondary securement strap) over top of the grey loop Velcro and press firmly together. ← 440

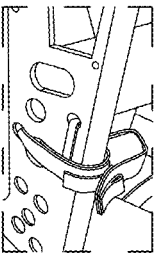
5. The restraint assembly should fit snug on stretcher and should not move during daily stretcher operation. If anchor becomes loose, tighten by repeating step three. If restraint is loose, tighten black containment cover strap and use provided rubber band. ← 450

FIG. 10A

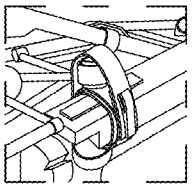
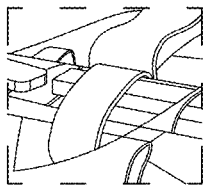
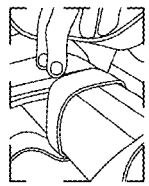
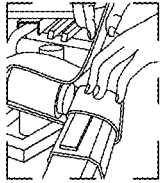
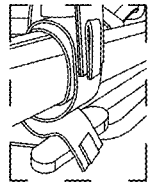
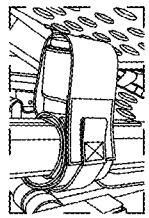

Completed installation of left wrist position. This position is located around the stretcher rail on the patients left side. — 500

1. Place the long loop Velcro end and secondary securement strap together. Feed both the loop Velcro and secondary securement strap all the way through the hole in the center mount bracket. — 510

2. Bring the same loop Velcro end out and around the left stretcher rail and position mid-way down rail on the inside. Continue to hold this position through step 3. — 520

3. While holding the long looped Velcro end, tightly pull the short hook Velcro over connecting the two sides. Press firmly to join the black hook and black loop Velcro together. — 530

4. Once tightly secured, join the grey hook Velcro (secondary securement strap) over top of the grey loop Velcro and press firmly together. — 540

Installation Complete — 550

FIG. 11A

LIMB RESTRAINT

This application claims the benefit of U.S. Prov. App. Ser. No. 62/503,821, filed by David Dufek, entitled LIMB RESTRAINT, on May 9, 2017, which is incorporated by reference herein in its entirety.

BACKGROUND

Medical limb restraints are used in connection with sedated, combative or agitated patients, to secure their wrists or ankles when emergency care is needed. When a patient is immobile, treatment can be administered safely and more effectively. These devices prevent patients from disrupting emergency treatment provided by healthcare providers in the field or hospital setting. Limb restraints prevent patients from dislodging various medical devices, such as endotracheal tubes, IV, or intravenous catheters, to name only a few.

Limb restraint devices used in connection with patient care are generally limited in use because they have no pre-determined connection points on which to apply to the stretcher and consequently are stored separate from the stretcher. Because traditional limb restraint products are separate from stretchers, they are often stored in drawers and medical bags so locating them can be a time-consuming task.

While some limb restraints products on the market can be pre-connected or tied to the stretcher, doing so would possibly limit the stretcher functions because the restraint or restraints could interfere with day-to-day stretcher operation. For example, you would have lengths of strap or Velcro that would be external of the stretcher dragging or possibly catching another object and further possibly blocking the folding of the side rails of the stretcher. Furthermore, these restraints can become contaminated, as they are not protected from damage, or biological matter, vomit, blood, etc.

Another drawback is that traditional restraints need to be looped or tied to the external structure in order to be attached and are not designed to be pre-connected to the stretcher prior to a person needing to be restrained. Having this design you must take both hands off patient or enlist the help of more providers, thereby increasing the chances of risk and delaying patient care.

Therefore, a need exists in the field for a limb restraint device capable of being secured beforehand on a stretcher, without tying knots or looping straps, so that its deployment and application can be done faster and, further, so it does not interfere with the normal or emergency operation of a stretcher.

Another need exists to have the restraint operated or tightened with one hand, so you can have another hand on the patient, utilizing strap slide hardware so that the length of line between the cuff and the stretcher can be shortened by pulling the free end of the line or handle.

BRIEF SUMMARY OF INVENTION

The present invention comprises a limb restraint system that is designed to be custom fitted and built-in to a person support apparatus, such as a patient support apparatus, including an emergency medical cot or stretcher, which provides one or more safe anchor locations in which limb restraints can be stored. The restraint includes a wrist or ankle cuff and a tether to which the cuff is secured on one end. The other end of the tether is mounted, optionally releasably and/or adjustably mounted, to an anchor that is configured to mount the restraint system to the person support apparatus. The cuff and tether are stored in a cover, and preferably in a compact configuration, such as in a folded configuration, ready for deployment therefrom, which protects the cuff and tether from contamination, for example, body fluid, or dirt and debris.

In one embodiment, a restraint system includes a restraint assembly and an anchor. The restrain assembly includes a tether, a restraint cuff coupled to said tether, and a frangible cover, for example a polymer film, operable to hold said tether and said cuff in a compact stowed configuration. The cover is sufficiently frangible or has a frangible portion to allow a person to manually tear open said cover. The anchor is coupled to said tether to releasably mount said restraint assembly to a component. When said cover is opened, said tether and said cuff are operable to be deployed from said stowed configuration and said cuff extended from said anchor.

In one aspect, the restrain system further includes a base, which couples said tether to said anchor.

In a further aspect, the base releasably couples said tether to said anchor.

In another aspect, the tether is releasably coupled to said base.

In yet another aspect, the cover encloses said tether and said cuff on said base.

According to another aspect, the tether comprises a strap.

Optionally, in any of the above, the restraint system may also include a securement strap. The securement strap has a first end joined with said anchor and a second free end operable to extend over said cover and said tether and cuff when in their compact stowed configuration and to couple to said anchor to thereby secure said cover and said tether and said cuff in their stowed configuration.

In one aspect, the securement strap includes a loop to provide a gripping surface for a person to pull on said securement strap.

In any of the above, the anchor comprises a strap. Optionally, the strap includes hook and loop strips for securing said strap in a loop configuration for securing said anchor about the component.

In any of the above, the tether includes an adjustment mechanism, and with the cover being operable to enclose at least a portion of said tether and said cuff.

For example, the tether may include an upper portion coupled to said cuff and a lower portion coupled to said anchor, with the adjustment mechanism operable to releasably couple said upper portion to said lower portion.

In a further aspect, the lower portion is releasably coupled to said anchor.

In yet another embodiment, a restraint assembly includes a tether, a restraint cuff coupled to said tether, and a frangible cover operable to hold said tether and said cuff in a compact stowed configuration, which is sufficiently frangible or has a frangible portion to allow a person to manually tear open said cover and allow said tether and said cuff to be deployed from said stowed configuration.

The present invention relates to a novel limb restraint device and apparatus for storage onto an external object. More particularly, the invention relates to a device that is capable in making wrist or ankle restraints more readily available, sanitary and pre-attached or easily attached to an external structure or medical stretcher rail.

BRIEF DESCRIPTION OF THE DRAWINGS

FIG. 10A is a flowchart of the installation steps for installing the restraint system to the head end section of the cot deck;

FIG. 11A is a flowchart of the installation steps for mounting the restraint system to the rail of the cot;

The present disclosure of a restraint system will now be described fully hereinafter with reference to the accompanying drawings, in which preferred embodiments of the disclosure are shown. The restraint system may, however, be embodied in many different forms and should not be construed as limited to the embodiments set forth herein. Rather, these embodiments are provided at exemplary only and not intended to limit the scope or interpretation of the claims listed below. T hose of ordinary skill in the art will realize that the following embodiments are illustrative and are not intended to be limiting in any way. Other embodiments will readily suggest themselves to such skilled persons having the benefit of this disclosure.

Throughout this specification, the present disclosure may be referred to as relating to restraining patients but it will be appreciated that this terminology is only illustrative and does not affect the scope of the invention. For example, the present disclosure may just as easily relate to restraints and restraint devices used in law enforcement, mental and behavioral health treatment, not just the medical field. Additionally, a person of skill in the art will appreciate that the use of restraints or cuffs within this disclosure is not intended to be limited to any specific form of restraint or cuff, and should be read to apply to all forms of restraints and/or cuffs in general. Accordingly, skilled artisans should not view the following disclosure as limited to any particular restraint device, and should read the following disclosure broadly with respect to the same.

In this detailed description, a person skilled in the art should note that directional terms, such as "above," "below," "upper," "lower," and other like terms are used for the convenience of the reader in reference to the drawings. Also, a person skilled in the art should notice this description may contain other terminology to convey position, orientation, and direction without departing from the principles of the present invention.

DETAILED DESCRIPTION

Figure 1:
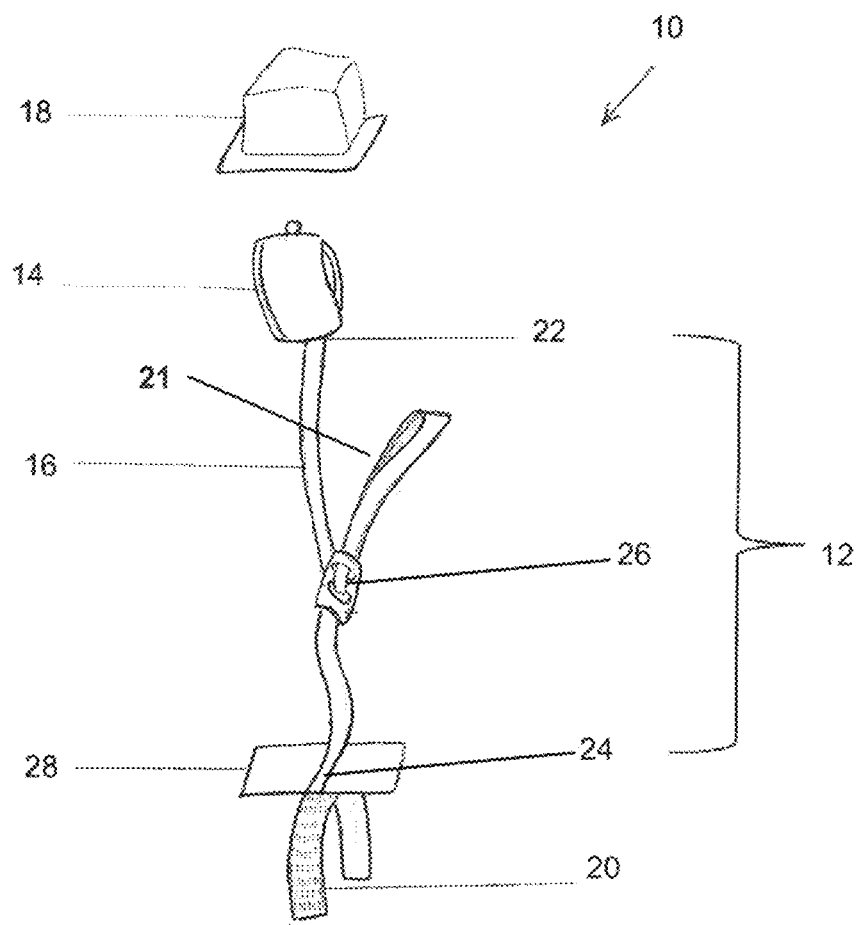
FIG. 1 is an exploded perspective view of the restraint system.

Referring to FIGS. 1-7, the numeral 10 generally designates a restraint system according to an embodiment of the present disclosure. As best seen in FIG. 1, restraint system 10 includes a restraint assembly 12, which includes a restraint cuff 14 (such as a wrist cuff or leg cuff), a tether 16, and a cover 18, and an anchor 20 to mount restraint assembly 12 to a person support apparatus, as noted, such as a patient support apparatus, including a cot, a stretcher, a bed, a chair, such as a wheelchair or a stair chair, or other patient transport apparatuses, including a back board as noted below. As will be more fully described below, cover 18 encloses cuff 14 and tether 16 (and optionally an adjustment mechanism) to protect them from bodily fluids and/or dirt and debris.

Tether 16 is coupled on one end to cuff 14, as noted by an optional coupler 22, and coupled at its other end to anchor 20, which as noted is configured to mount restraint assembly 12 to a person support apparatus. Optionally, tether 16 is coupled to cuff 14 by a releasable coupler 22 to allow removal of the cuff 14 for cleaning or replacement. Coupler 22 may comprise a hook and loop fastener or fasteners, such as VELCRO; a carabiner; a clamp; a clip, such as an r-clip; a shackle; a pin, such as a linchpin, split pin, a tapered pin; a lobster clasp; a fastener, such as a screw, a bolt, or a rivet or the like; a magnet; or any other coupler understood by those skilled in the art. In the case of hoop and loop fasteners, such as VELCRO strips, one strip may be mounted to the end of tether 16 and the other mounted to the cuff 14. Further, coupler 22 may comprise VELCRO strips with a double lock configuration, such as shown in U.S. Pat. No. 5,076,288, which is incorporated by reference here in its entirety and allows for an even stronger coupling between cuff 14 and tether 16.

Additionally, tether 16 may include a coupler 24, such as a releasable coupler, between tether 16 and anchor 20. Similar to coupler 22, a suitable coupler may comprise hook and loop fastener or fasteners, such as VELCRO; a carabiner; a clamp; a clip, such as an r-clip; a shackle; a pin, such as a linchpin, split pin, a tapered pin; a lobster clasp; a fastener, such as a screw, a bolt, or a rivet or the like; a magnet; or any other coupler understood by those skilled in the art. In this manner, part or all of restraint assembly 12 may be removed for cleaning or disposal. Alternately, depending on the type of coupler, releasable coupler 24 may be provided to directly releasably mount restraint system 10 to medical equipment, such as a stretcher or other patient transport apparatuses, as more fully described below. In addition, tether 16 may include an adjustment mechanism 26, such as a buckle or strap slide, which allows the length of the tether 16 to be adjusted.

Figure 2:
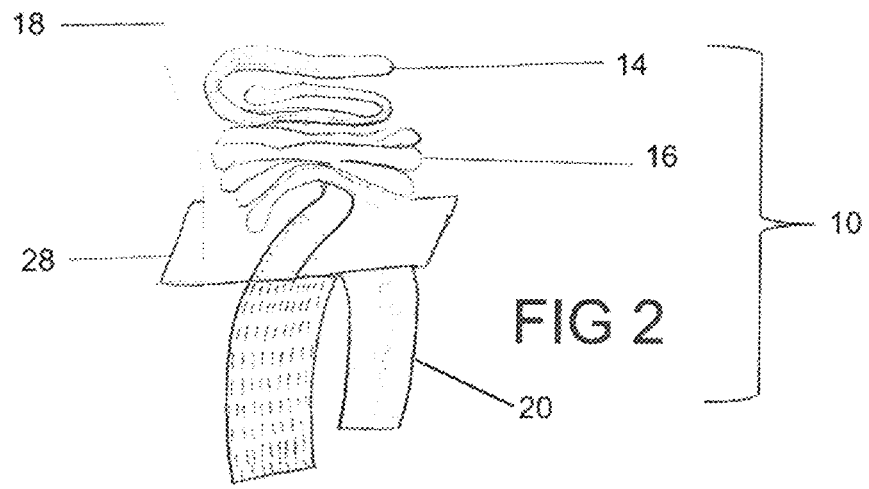
FIG. 2 is a partial fragmentary view of the restraint system showing how the cuff and tether are folded within the cover.
Figure 3:
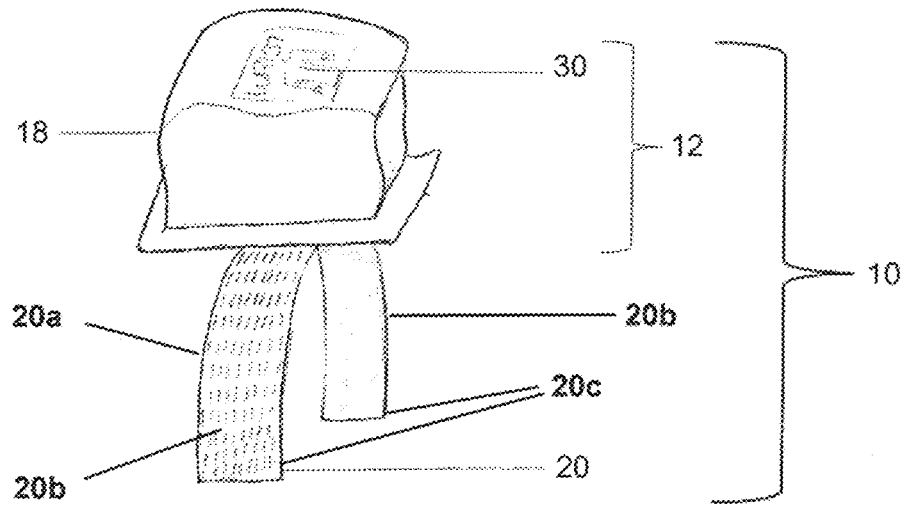
FIG. 3 is a perspective view of the restraint system with its restraint assembly in a non-deployed state or compact configuration illustrating the cuff and tether stored within the cover.

Referring to FIG. 2, in the illustrated embodiment, when not in use and reconfigured in its non-deployed configuration, cuff 14, tether 16, and adjustment mechanism 26 are configured in a compact configuration, such as by folding tether 16 and cuff 14 and then enclosing it inside cover 18. Cover 18 may completely contain and enclose cuff 14, tether 16, and adjustment mechanism 26 and, further, form a sealed enclosure. For example, cover 18 may be formed from a polymer bag or film, such a thin plastic film, which is easily opened, for example, by tearing. Optionally, cover 18 may incorporate a release or an assist mechanism, such as a rip cord, or may have one or more regions of reduced thickness to form a tear strip or strips or the like. In this manner, cover 18 is a frangible cover that can either be manually broken open without or with assistance (e.g. on the form of a rip cord or weakened regions of the material forming the cover). The term "frangible" is used broadly herein to mean something that can be broken or torn manually with or without the assistance noted above. In another embodiment, cover 18 may require a tool to break or tear the cover a part.

In one embodiment, cover 18 encloses cuff 14, tether 16, and adjustment mechanism 26 over a base 28, with cover 18 mounted over the folded cuff 14, folded tether 16, and adjustment mechanism 28 and secured to base 28 to thereby enclosing cuff 14, tether 16, and adjustment mechanism 26 between cover 18 and base 28. Second coupler 24 may be then connected to base 28, for example permanently or releasably, which then can be used to mount restrain assembly 12 to anchor 20. Optionally, as described below, the cover may enclose only a portion of the tether and cuff.

In the illustrative embodiment, anchor 20 comprises a strap 20a with a releasable fastener or fasteners 20b on its ends 20c, such as hook and loop fasteners, including VELCRO strips, that allow the strap to wrap around a portion of the person support apparatus, more fully described below, and then be secured in place once the fasteners are joined together. Optionally, the fasteners on strap 20a may comprise VELCRO strips with a double lock configuration, such as shown in U.S. Pat. No. 5,076,288. In another embodiment, as more fully described below, the anchor may comprise a strap that extends around or loops through a portion of the person support apparatus and may be secured thereto using a buckle or other mechanical fastening mechanisms.

In one embodiment, cover 18 is integrally formed with base 28 (and therefore base 28 forms part of the cover) so that cover 18 includes the base. In this manner, connector 24 is, therefore, mounted to the cover 18.

Figure 4:
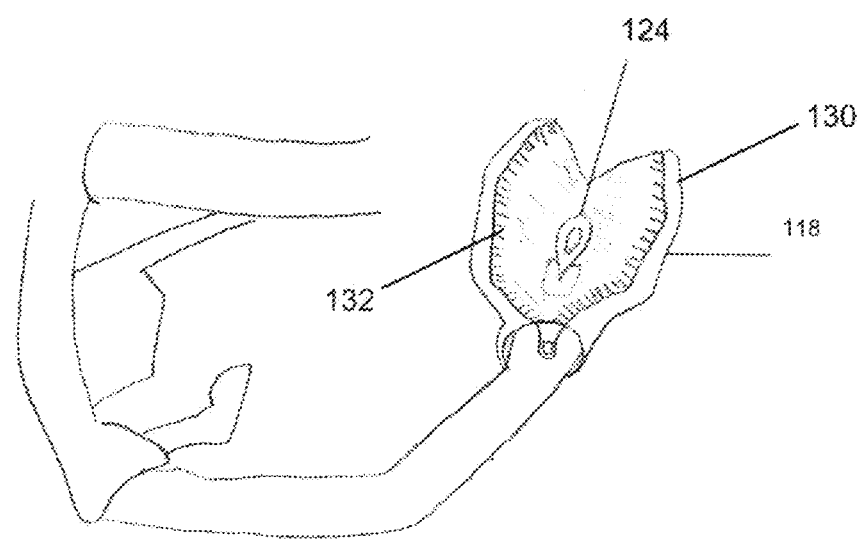
FIG. 4 is a perspective view of another embodiment of an anchor for mounting a restraint assembly to a person support apparatus in the form of a cot.
Figure 5:
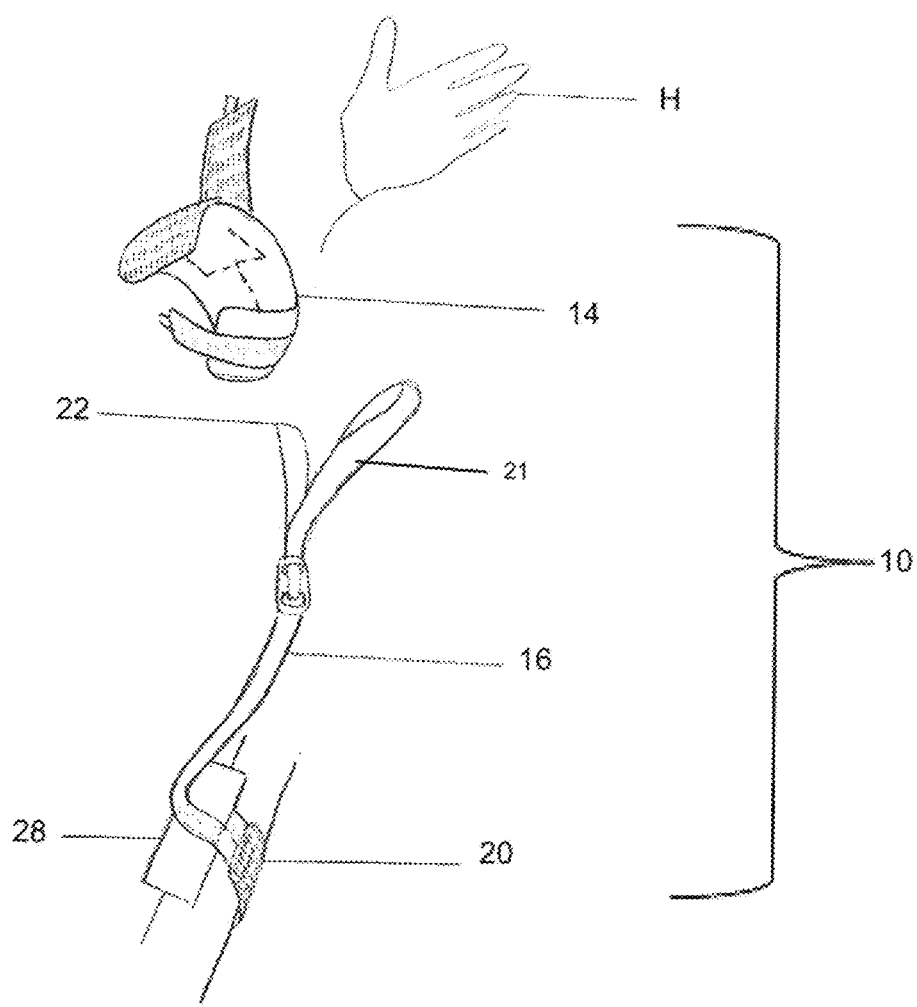
FIG. 5 is another exploded perspective view of the restraint system with the restraint assembly deployed from the cover and further with the cuff detached from the tether.

In another embodiment, as best seen in FIG. 4, the restraint assembly (not shown) may secure to a person support apparatus using a coupler 124 that is permanently attached (i.e. at least not releasable without a tool or disassembly) to a person support apparatus and includes a loop or ring for attachment of the restraint assembly (e.g. tether 16, cuff 14, and adjustment mechanism 26) to coupler 124 so that the tether and the cuff may be removed from coupler 124 for cleaning or replacement, while still allowing the tether and the cuff (and the adjustment mechanism) to be deployed as noted. Furthermore, this pre-attached deployment method is designed so the restraint assembly 12 is ready to go when a person becomes combative, and is stored out of the way but then easily deployed from one or more pre-determined connection points. Alternately, the restraint assembly may be decoupled from the person support apparatus and then coupled to the person support apparatus one or more pre-determined connection points when needed.

In the illustrated embodiment, coupler 124 comprises a ring or loop and may be enclosed by a cover 118, when the restraint assembly is removed, which includes a closeable opening which when opened allows access to coupler 124. Cover 118 may be closed by a closure mechanism 132, such as a zipper or Velcro strips, to allow the coupler 124 to be enclosed and protected. Optionally, cover 118 may be padded to provide protection to a person supported on the person support apparatus or to someone handling the person support apparatus from the coupler 124 when the coupler is formed from a rigid loop or ring, for example. Alternately, coupler 124 may simply comprise a hook and loop fastener that is glued to the person support apparatus. As would understood, therefore, restraint assembly system 10 may be mounted to a person support apparatus, such as a cot, a stretcher, a bed, a chair, or other object, via, for example, base 28 or via anchor 20 or coupler 124.

Therefore, the person support apparatus may be constructed to include the coupler 124 and may, as noted, be selectively and releasably coupled to the restraint assembly via an anchor, such as anchor 20, or releasable coupler 24. Additionally, a piece of rubber, plastic, foam, cloth, fabric, or other non-metallic object may be interposed between coupler 124 and the restraint assembly, such as restraint assembly 12, or between base 28 and the person support apparatus to reduce the noise, friction, stress and/or damage on the restraint assembly 12, and/or person support apparatus.

Referring again to FIGS. 1 and 3, cover 18 may be formed into any shape, including any cubical or tubular shape, including a square, rectangle, circle, ovoid, triangle, or any other polygon, using a vacuum sealing technique or RF welding.

For example, and without limitation, the second coupler 24 (or coupler 124), as noted, may attach to the external structure of the person support apparatus, for example, using an adhesive, such as glue or hook and loop fasteners, such as VELCRO; a carabiner; a clamp; a clip, such as an r-clip; a shackle; a pin, such as a linchpin, split pin, a tapered pin; a lobster clasp; a fastener, such as a screw, a bolt, or rivet or the like; a magnet; or by welding any other method of securement or mounting understood by those skilled in the art.

The second coupler 24 or coupler 124 may further be adjustable to more advantageously attach to many different objects or designs of person support apparatuses. Additionally, the person support apparatus mounting structure may include an eyelet; grommet; hook and loop fasteners, such as VELCRO, or other coupling mechanism or engagement structure.

As another example and without limitation, the restraint assembly 12 or a portion of the restraint assembly 12, may be integrated into the person support apparatus. The term integrated as used herein refers to the restraint assembly being formed part of the person support apparatus where its removal would require the use of a tool or disassembly. As noted above, second coupler 24 or coupler 124 may be integrated into the person support apparatus through molding, integrally molding, over molding, glue, adhesive, fastener, screw, bolt, welding, or any other means understood by those having the benefit of this disclosure. In this example, the second coupler 24 or coupler 124 may permanently connect to the restraint assembly 12 to the person support apparatus.

As noted above, cover 18 may be a polymer such as plastic, or may comprise a synthetic fiber, paper or anything else that can encase or protect the cuff 14 and tether 16, while minimizing contamination risk. Cover 18 may be tapped, or glued to base 28, thereby holding the entire restraint system 10 or restraint assembly 12 together. The cover 18 may be permanently attached to base 28 and used an anchor to secure cover 18 to the base (e.g. as noted above via heating sealing or welding), which will allow for the cuff 14 and tether 16 to be connected or disconnected from the base or the anchor.

Optionally, cover 18 may double as a permanent storage case, which can be separated from cuff 14 and tether 16, and may be reusable or disposable. It should be understood that cover 18 and base 28 are customizable so it will fit several different person support apparatuses, and further fit different components or mount to different components on the person support apparatuses. Second coupler 24 or coupler 124 may be quickly disconnected allowing removal of the entire restraint assembly where cleaning, disposal, damage, cutting or transfer to other person support apparatuses, such as a cot, stretcher, or backboard, is needed.

In operation, once deployed the restraint assembly can be attached to a person's ankle or wrist, using cuff 14. Once the person's wrist, or ankle, is secured with cuff 14, tether 16 can be adjusted or tightened by using the end of the tether, such as a looped end of the tether that forms a handle (21). This easy one handed design can be accomplished by using adjustment mechanism 26 in the form of a strap slide, which holds automatically when slack is taken through it. The cuff 14 and tether 16 can be made from cotton, synthetic strap or cloth materials, coated webbing, rope, cables, rubber, snap bracelets, magnets or paper and may include one or more hook and loop fasteners, such as VELCRO strips.

Those skilled in the art will appreciate that although anchor 20 is illustrated as being a strap with hook and loop fasteners, such as VELCRO strips, the connection between the restraint assembly 12 and the person support apparatus may be provided by any means available in the art and by one or more connections. Specifically, the connection may be provided by a pivot joint, a ball and socket joint, a rotational joint, a knuckle joint, a turnbuckle, a strap without hook and loop fasteners, and/or a pin joint, but any joint understood by those having the benefit of this disclosure may be used. The base 28 may also be connected to the second connector 24 using a combination of a neck and a joint as described herein. The neck could be flexible and may be steel, metal, metal alloy, plastic, nylon, synthetic material, fibrous material, or other similar material understood by those having the benefit of this disclosure. For example, and without limitation, the neck may be a modular hose system, such as an adjustable hose with a steel cable inserted within the hose. This may also advantageously allow base 24 to be positioned in a location away from the person support apparatus, and allow the restraint system 10 or restraint assembly 12 to attach to many different objects or designs of person support apparatuses.

The deployed or extended position may be defined as the tether 16 being extended from base 28 and out of the cover 18 so as to be able to be connected to a person supported on person support apparatus or vice versa depending on whether the cuff is first applied to the person or whether the restraint assembly is first coupled to the person support apparatus. Further, where the cuff 14 is initially decoupled from the tether and then placed on the person's appendage, the deployed or extended position of the tether 16 is meant to allow the coupler 22 to then be connected to the cuff 14.

As noted above, tether 16 may include an upper portion be connected to a portion of the adjustment mechanism 26, such as a strap slide, and may extend there through to form a handle or pull, which is easy to grasp and which facilitates adjustment of the length of tether 16.

In addition, as noted above, tether 16 may be adapted to be detachably connected to cuff 14 and/or base 28. Either coupler 22 or 24 may further be capable of rapid disengagement of tether 16 from the cuff or the base, such as when in the form of a clip, a carabiner, or any other type of connector described above that may allow for engagement by a user with one hand to readily move the connector from a closed position to an opened position so that, when in the opened position, the tether can be removed.

In one embodiment, anchor 20 comprises a strap that can be wrapped 360 degrees around a portion of the person support apparatus. The base 28 optionally has a flat backing that can be attached to anchor 20 (for example, by stitching or glue or using hook and look strips) and allows restraint assembly 12 to be stored in upright position on base 28 (see FIG. 3), and contained within cover 18 ready for deployment. Once deployment is necessary, the cover 18 is opened, and then tether 16 and cuff 14 can be extended toward the patient. Once the cuff 14 is placed on a person's anatomy, the handle 21 may be pulled tight to remove slack thereby positioning patient correctly. Once attached, this restraint system 10 features a quick release function. This can be achieved by loosening tether 16, removing cuff 14 from a patient's anatomy, or disconnecting the base 28 or anchor 20. It should be understood therefore, restraint system 10 or restraint assembly 12, can either be pre-connected to the person support apparatus, or placed there in time of need.

In one embodiment, cover 18, cuff 14, or base 28, may include a label 30 indicating intended use of the cuff and, optionally, may include simple to follow instructions or illustrations for application, and warnings. These instructions may also struck a user on where to position the restraint system or restraint assembly on the person support apparatus and further how to use the restraint system 10 or restraint assembly 12.

Figure 6:
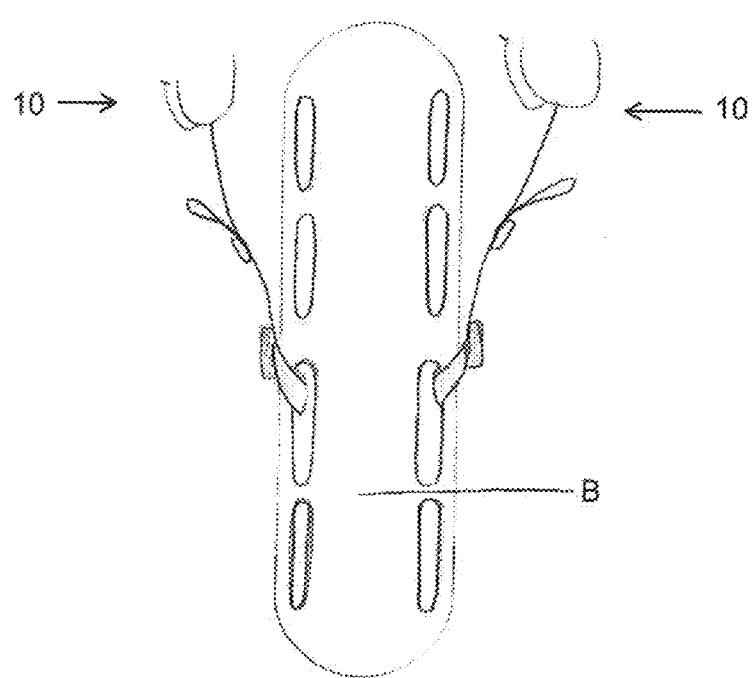
FIG. 6 is a plan view of the restraint system mounted on a backboard.

Referring to FIG. 6, in one embodiment, the restraint system 10 may be attached to a backboard B. In this particular embodiment, restraint system 10 optionally includes an anchor 20 formed from Velcro straps. For example, when the base 28 is formed from a fabric, the Velcro straps may be sewn to base 28 so that it can be fitted to several different sized person support apparatuses, such as illustrated backboard and cots or stretchers. As described above, the cover for restraint system 10 may be formed into any cubical or tubular shape, including a square, rectangle, circle, ovoid, triangle, or any other polygon.

Figure 7:
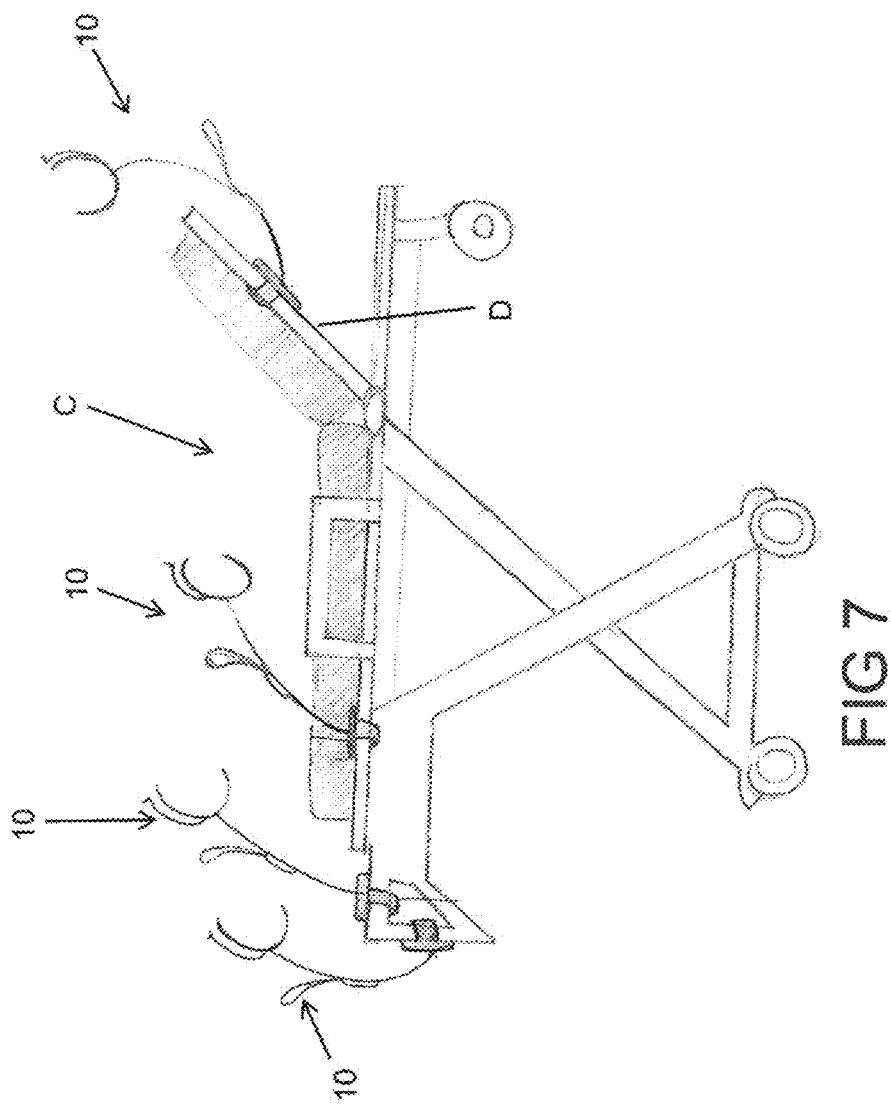
FIG. 7 is side view of a patient support in the form of a cot with four limb restraint assemblies mounted and in their deployed state.

Referring to FIG. 7, in one embodiment, the restraint system 10 may be attached to a deck D of a cot C. In this embodiment, restraint system 10 optionally also includes an anchor 20 formed from a strap with VELCRO strips. Unlike the prior art, restraint assembly 12, therefore, may be already attached, contained and secured within cover 18, in predetermined locations around the patient support, such as the head section of the cot deck, the rails of the cot, and/or the foot end of the cot, which can avoid incorrectly positioned attachment points on the person support apparatus.

Figure 8:
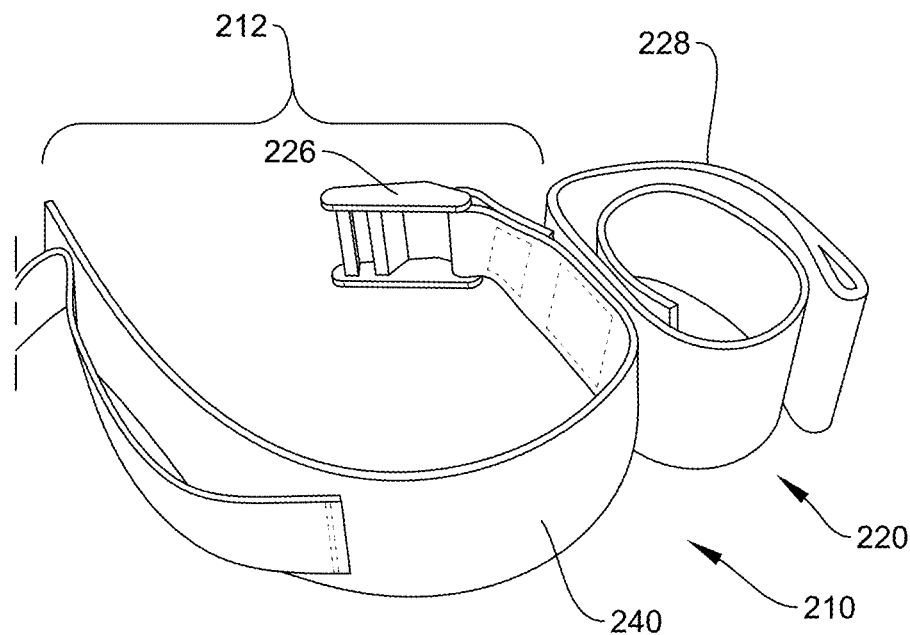
FIG. 8 is a perspective view of another embodiment of the restraint system incorporating a securement strap over the cover of the restraint assembly.
Figure 9:
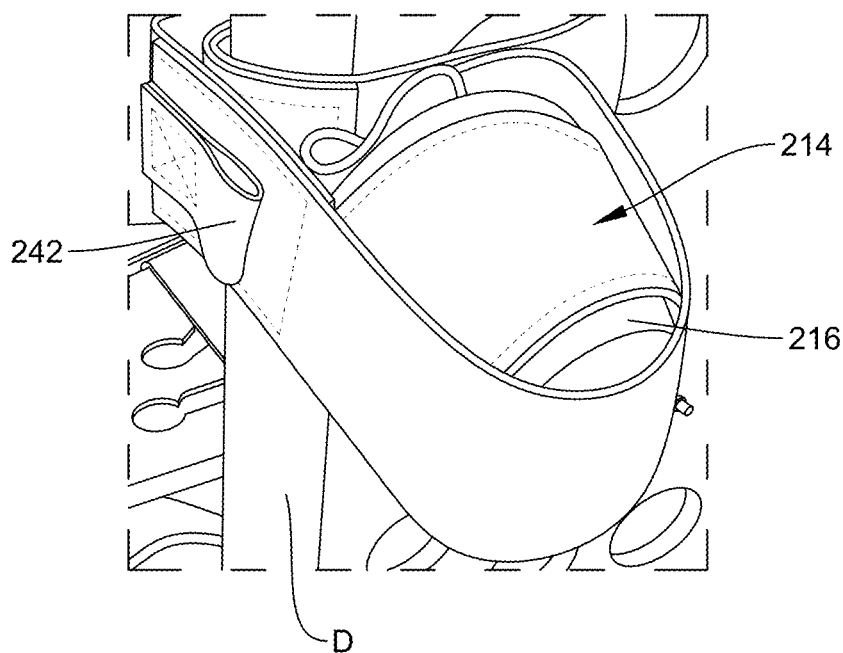
FIG. 9 is a perspective view of the restraint system of FIG. 8 shown mounted to a head section of a cot deck.

Referring to FIGS. 8 and 9, the numeral 210 generally designates another embodiment of the restraint system. Restraint system 210 may be of similar construction to restraint system 10 and includes a restraint assembly 212, which includes a cuff 214 and a tether 216 (FIG. 9), and an anchor 220. Anchor 220 releasably mounts the restraint assembly 212 to a person support apparatus, for example, a cots, such as shown in FIGS. 10-14. Although illustrated as a strap with at least two VELCRO strips, anchor 220 may take on other forms, such as those described above in reference to the previous embodiments.

In the illustrated embodiment, restraint assembly 212 includes a securement strap 240. Securement strap 240 may form a base 228 to which anchor 220 is secured or may be secured to anchor 220, for example by stitching or glue. In the illustrated embodiment, securement strap 240 is secured to anchor 220 on one side of restraint assembly 212 and includes a loop 242 (which forms a pull tab) and a releasable coupler, such as a hook and loop strip, for releasably engaging the anchor 220 on the other side of restrain assembly 212 (so that it straddles restrain assembly 212). Securement strap 240, therefore, helps keep the restraint assembly 212 in its folded compact configuration on anchor 220. Tether 216 and cuff 214 may be mounted to anchor 220 using VELCRO strips or other suitable couplers, as described above, or may be secured thereto by stitching.

In the illustrated embodiment, tether 216 includes an upper portion, which is coupled to the cuff, and a lower portion that is coupled to anchor 220, which are releasably coupled together by adjustment mechanism 226, for example, a buckle, such as a cam buckle. In this manner, the upper portion of tether 216 and cuff 214 may be disconnected from the lower portion of the tether 216 for replacement or cleaning. Optionally, the lower portion of tether 216 may be secured to anchor 220, as noted above by stitching or glue. Alternately, the lower portion of tether 216 may be secured be releasably attached to anchor 220 using releasable fasteners, such as hook and loop fasteners, including VECLRO strips, so that the removable portion of the restrain assembly 212 comprises the cuff 214, both upper and lower portions of tether 216, and the adjustment mechanism 226.

Anchor 220 may also be formed from a strap with fasteners, such as hook and loop fasteners, including VELCRO strips, to allow the anchor 220 to be wrapped around a portion of the person support apparatus and secured thereto by forming a loop with the strap using the VELCRO strips.

Although not shown in FIGS. 8 and 9, restraint assembly 212 may also include a cover 218 (shown in FIGS. 15 and 16), to cover the folded or rolled up cuff 214 and tether 216, and optional adjustment mechanism. For further details of the construction of the cover, reference is made the above embodiments. Further, optionally the cover may also at least partially or fully enclose the securement strap. The orientation of the strap and cuff within securement strap 240 may vary. As shown in FIGS. 8 and 9, strap 216 and cuff 214 may be folded or wrapped around so that their edges are facing inwardly toward anchor 220 and securement strap 240.

Figure 15:
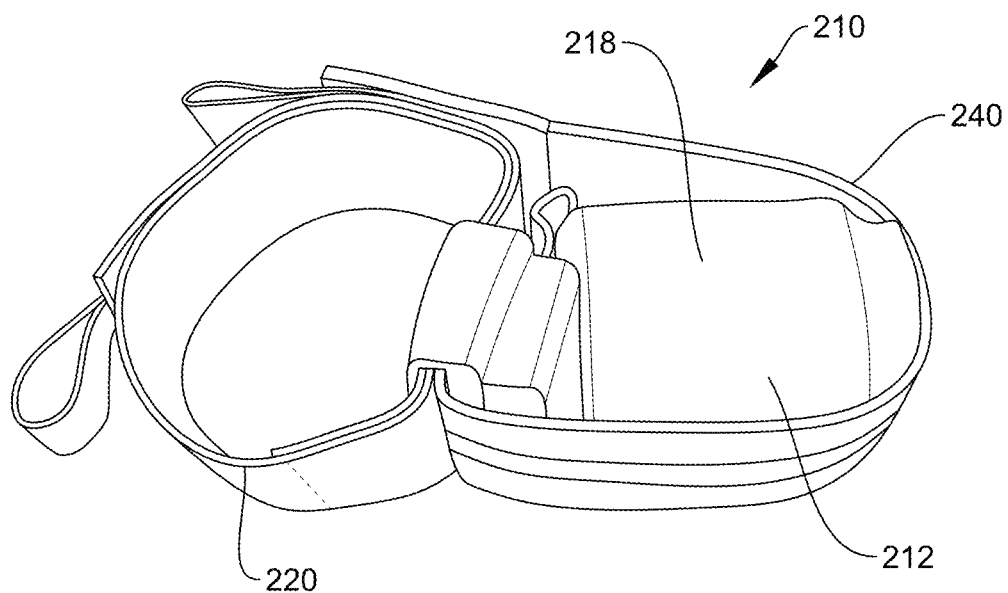
FIG. 15 is a perspective view of the restraint system of FIG. 8 but with the restraint assembly rotated ninety degrees in the securement strap.
Figure 16:
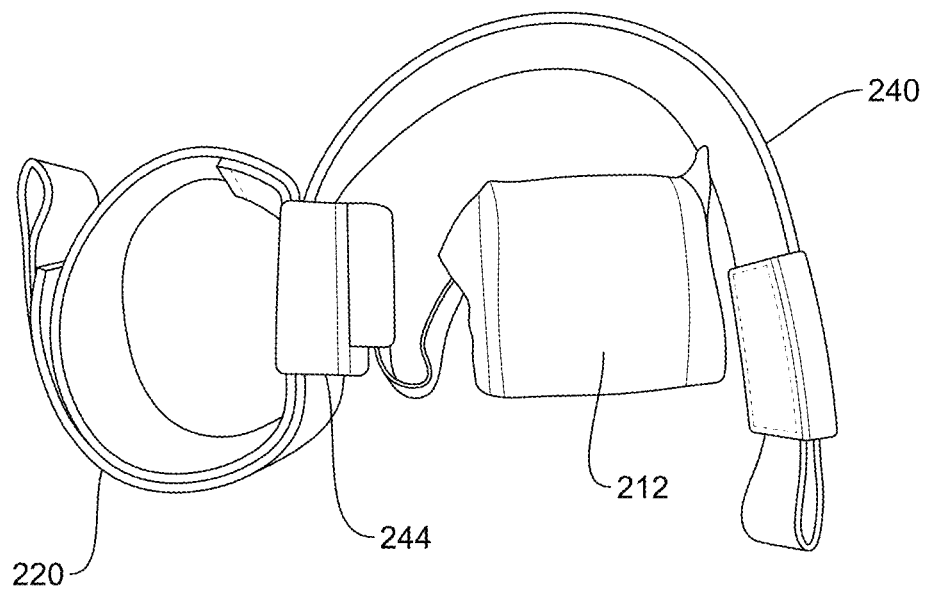
FIG. 16 is exploded side view of the restraint system of FIG. 15.

In the illustrated embodiment, adjustment mechanism 226 may be attached closer to anchor 220 (lower end of tether 216 may be relatively short) than in the previous embodiment and therefore may not be included in cover 218. Referring to FIGS. 15 and 16, adjustment mechanism 226 may be enclosed in an elastic band or loop 244 that is secured to anchor 220 and is extended over adjustment mechanism 226. Access to adjustment mechanism 226, therefore, may be achieved pulling back the elastic band 244, which then allows a user to adjust the length of the tether.

Figure 8A:
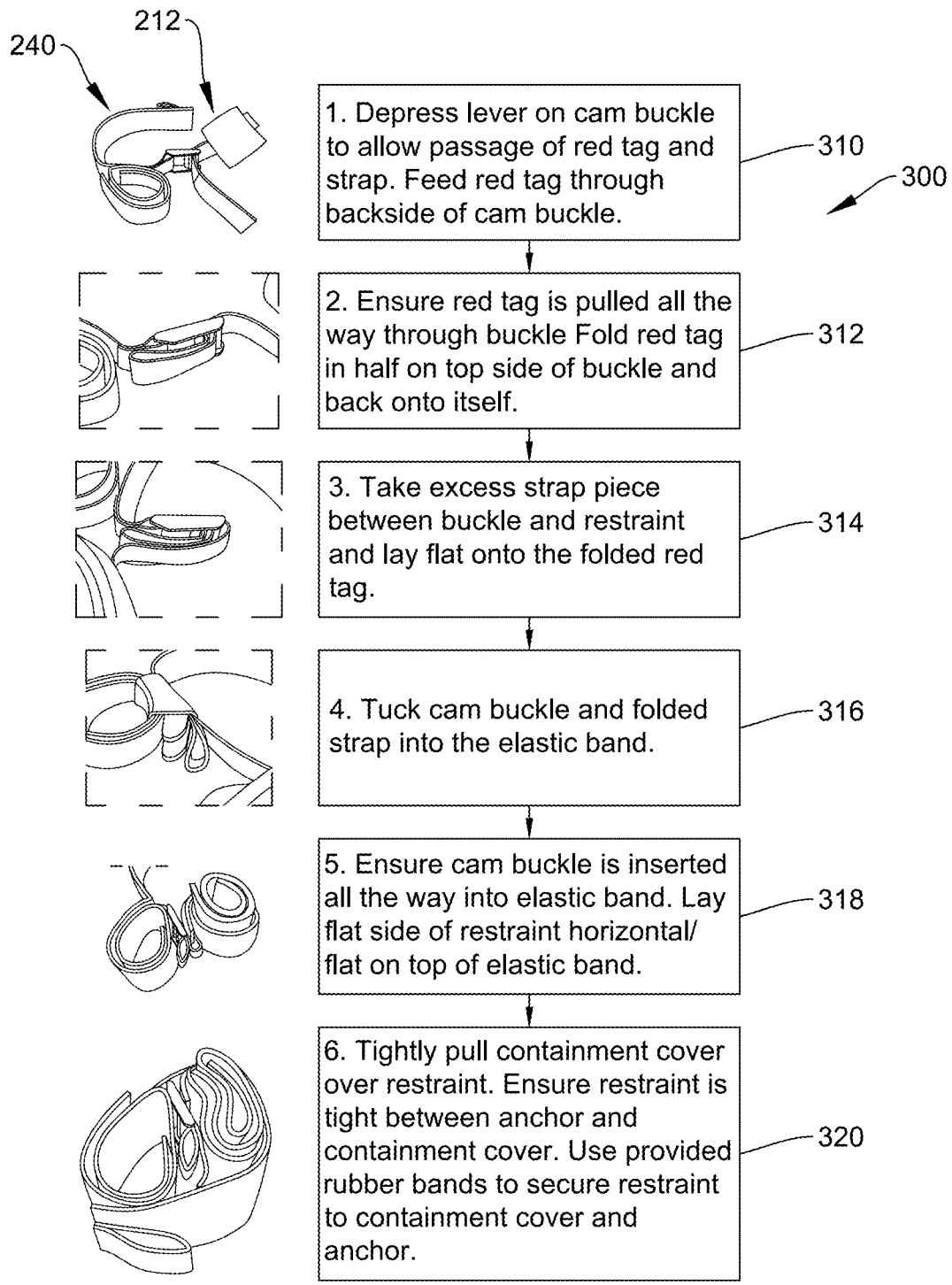
FIG. 8A is a flowchart of the steps for repackaging and storing the restraint assembly in the restraint system.
Figure 10:
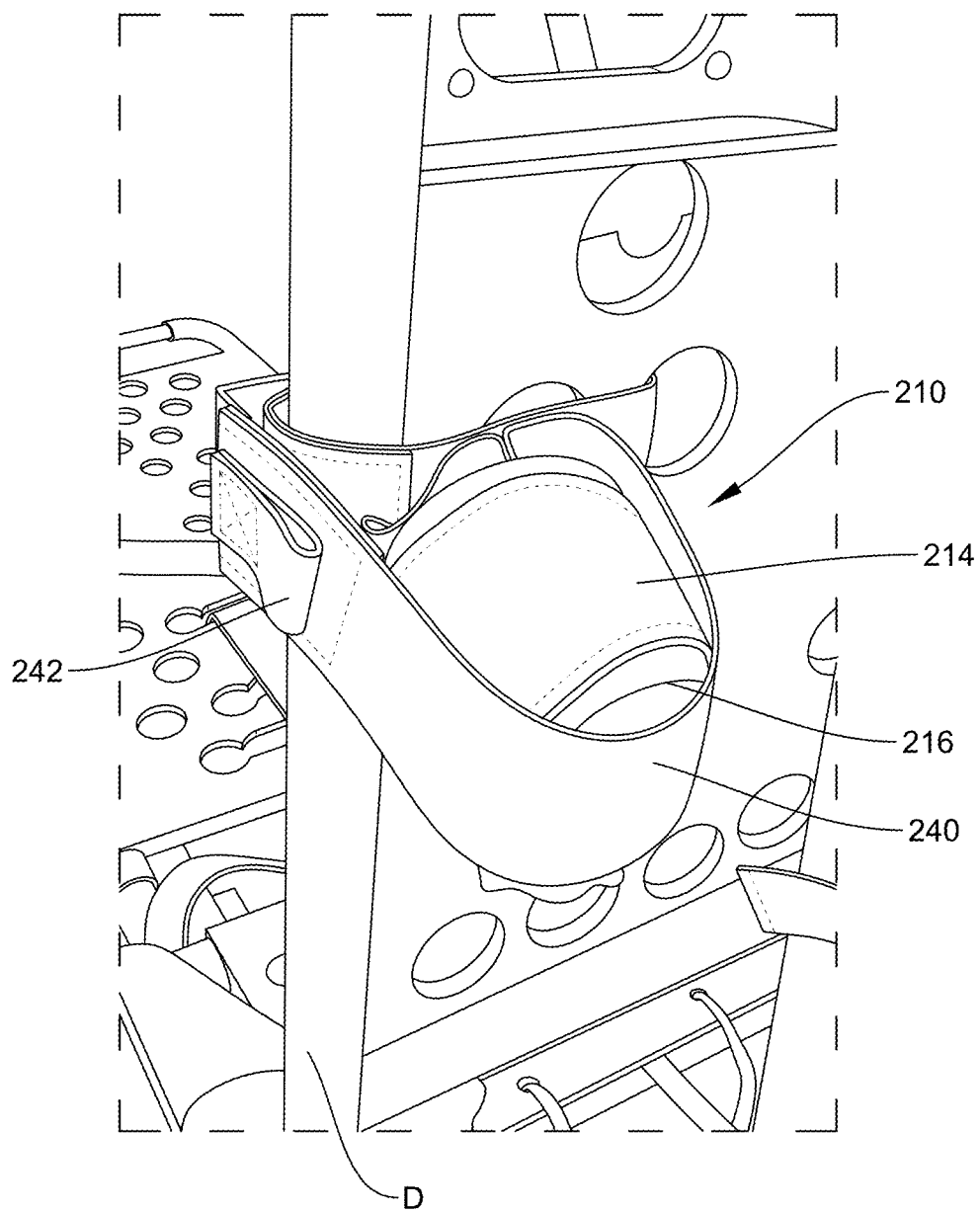
FIG. 10 is an enlarged perspective view of the restraint system of FIG. 8 shown mounted to the head section of the cot deck.
Figure 11:
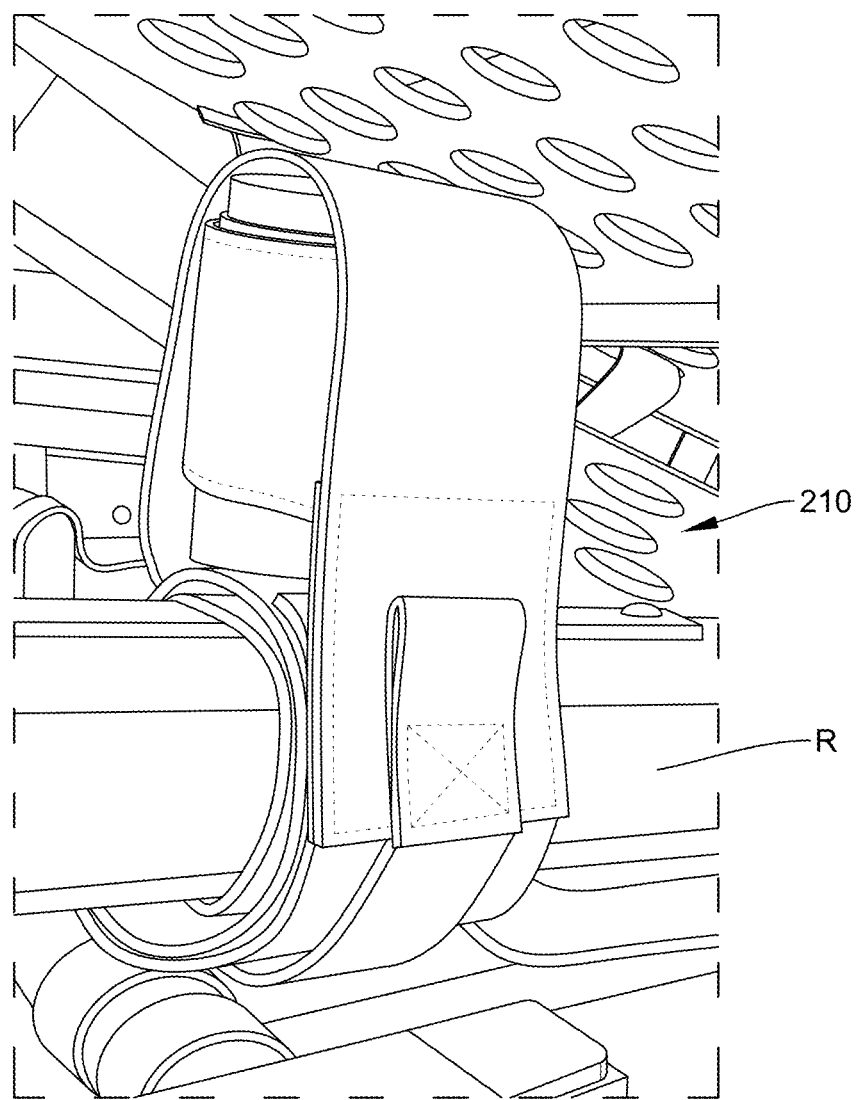
FIG. 11 is enlarged perspective view of the restraint system mounted to a rail of a cot.
Figure 13:
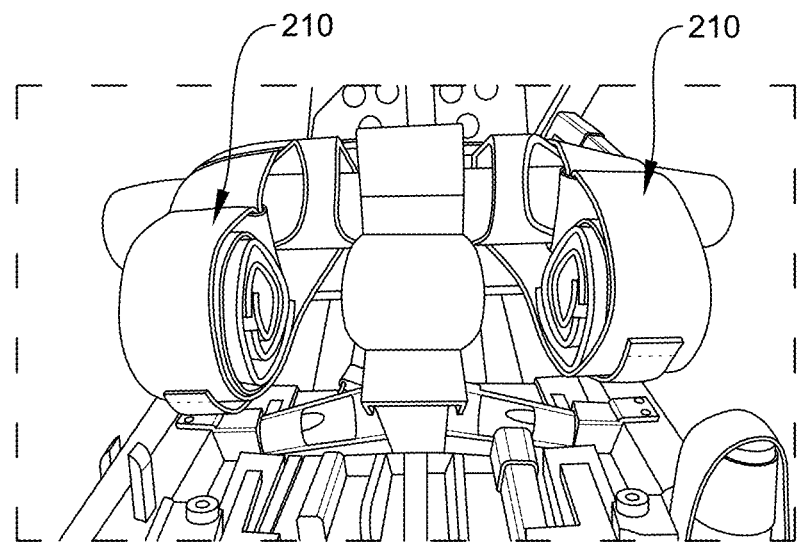
FIG. 13 is enlarged in view of the foot section of the cot deck of FIG. 12.

Referring to FIG. 8A, to complete assembly of the restraint assembly 212 (300) (when anchor 220 is mounted to a person support apparatus and, further, includes the lower portion of the tether 216 coupled to anchor 220, either integrally or releasably) the free end of the upper portion of the tether 216 is inserted into the release mechanism 226. In the illustrated embodiment, the release mechanism 226 comprises a cam buckle. Therefore, to couple the upper portion of tether 216 to its lower portion, a user initially depresses the lever on the cam buckle to allow the free end of the upper portion of the strap (which includes a red tag in the illustration) to be fed through the buckle (310). Once, a user ensures that the end of the strap with the red tag is pulled all the way through buckle, the red tag is folded in half on top side of buckle and back onto itself (320). The excess of the strap is then moved or taken between buckle and restraint and lain flat onto the folded red tag (330). Then the cam buckle and folded strap is tucked into an elastic band 244 (340) and inserted all the way into elastic band so that its flat side lays of top of elastic band 244 (350).

Then securement strap 240 is pulled over the restraint assembly 212 and optionally over the restraint system 210 (which includes at least part of the anchor) (360). To ensure restraint assembly is tight between anchor and the cover, elastic bands (not shown) may be used to secure restraint assembly to the securement strap 240 and the anchor 220 (360).

Referring to FIG. 10A, to install a wrist version of the restraint system (400), e.g. restraint system 210, to an emergency cot or stretcher, a user must first locate the proposed position on the head of the stretcher, for example, on the patient's left side (410). The long loop VELCRO end of anchor 220 is then placed together with the securement strap 240 (420). Both the loop Velcro end of anchor 220 and secondary securement strap 240 may then be fed all the way through the second hole on left side of stretcher ((410). The same loop end is then brought around the deck back to the edge of the first hole (430). Hold this position through the third step. While holding the long looped Velcro end of anchor 220, tightly pull the short hook Velcro of anchor 220 over to join and connect the two ends of the anchor together (440). Press firmly to join the two ends together (440). The securement strap 240 can then sit flush against the stretcher frame as shown in photo. Once tightly secured, join the VELCRO strip of the securement strap 240 over top of the VELCRO strip of the anchor 220 and press firmly together (450). The restraint system should fit snug on cot or stretcher and should not move during daily stretcher operation. If anchor becomes loose, tighten by repeating step 440. If the restraint assembly is loose, tighten the securement strap and optionally use an elastic band, such as a rubber band, over the securement strap 240 to increase the cinching of the restraint assembly.

Referring to FIG. 11A, to install another wrist restraint system (500), such as restraint 210, for example in the left wrist position, the user initially locates the proper position on the rail of the cot or stretcher on the patient's left side (510). Alternately, the left wrist restraint system may be mounted to the deck of the cot or stretcher similar to the procedure described above. The long loop VELCRO end of anchor 220 and securement strap 240 are placed together and fed all the way through the hole in the center mount bracket of the cot or stretcher below the rail. Pull the same loop Velcro end of the anchor out and around the left stretcher rail and position it mid-way down rail on the inside (520). Continue to hold this position through step 530. While holding the long looped Velcro end of the anchor 220, tightly pull the short Velcro end of the anchor 220 over and connect the two ends together. Press firmly to join the two Velcro ends together (530). Once tightly secured, pull the securement strap over the restrain assembly and join the Velcro strip on the securement strap 240 over top of the Velcro of the anchor 220 and press firmly together (540).

Figure 12:
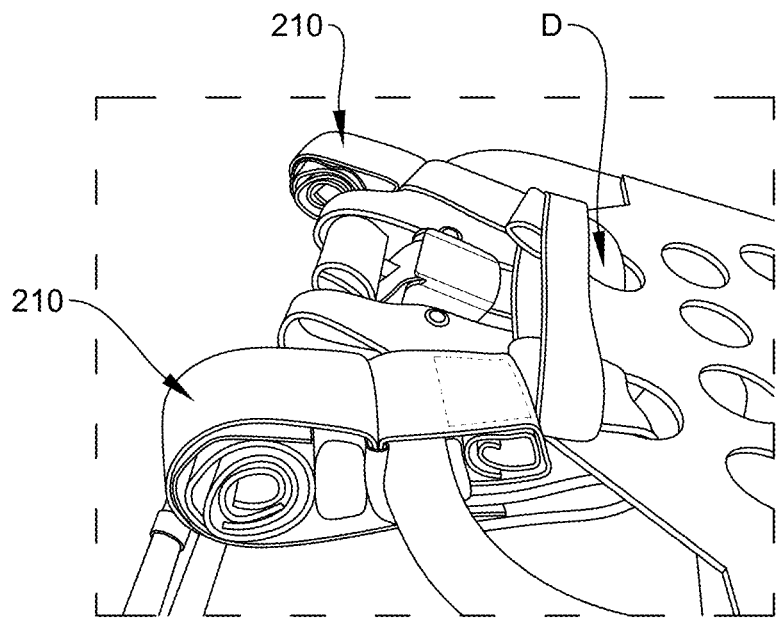
FIG. 12 is a perspective view of the foot end of the cot deck with a pair of restraint systems mounted to the foot section of the cot deck.
Figure 12A:
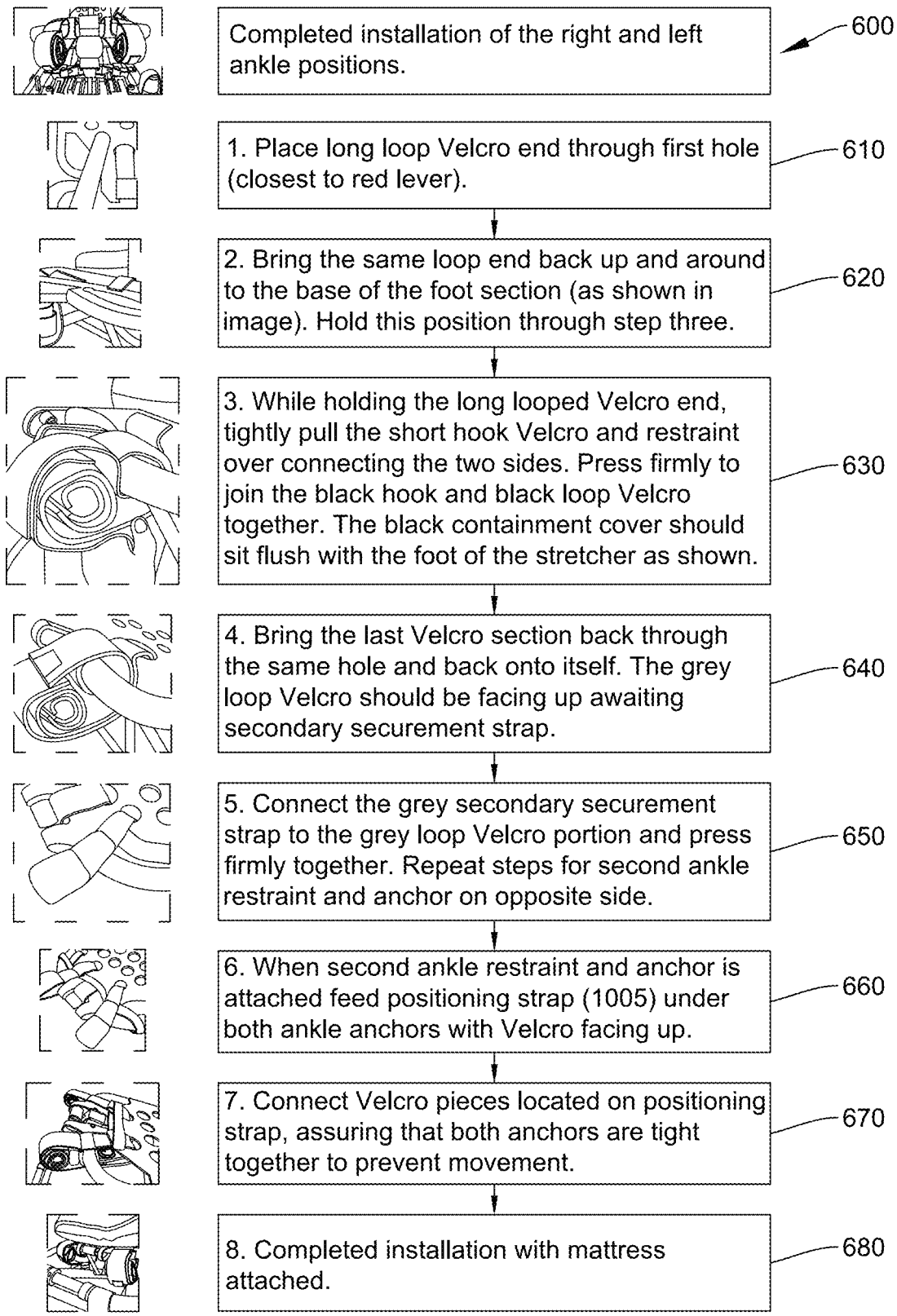
FIG. 12A is a flowchart of the installation steps for noting the restraint system to the foot section of the cot deck.

Now referring to FIG. 12A, to install right and left ankle restraints (600), such as restraint assemblies 210, place the long Velcro end of anchor 220 through one of the openings on one side of the foot section of the cot's or stretcher's deck (610). Pull the same long Velcro end of anchor 220 up and around to the base of the foot section (as shown in image). Hold this position through step 630 (620). While holding the long Velcro end of anchor 220, tightly pull the short Velcro end of the anchor 220 and restraint assembly 212 over, connecting the two ends of the anchor together (630). Press firmly to join the two Velcro ends together (630). The cover (not shown) can sit flush with the foot section of the deck of the cot or stretcher as shown. Then pull the last Velcro section back through the same hole and back onto itself. The grey loop Velcro should be facing up awaiting secondary securement strap (640). Connect the grey secondary securement strap to the grey loop Velcro portion and press firmly together. Repeat steps for second ankle restraint and anchor on opposite side (650). When second ankle restraint and anchor is attached feed positioning strap under both ankle anchors with Velcro facing up (660). Connect Velcro pieces located on positioning strap, assuring that both anchors are tight together to prevent movement (670). The installation is then complete when the mattress is then paced on the deck (680).

Figure 14:
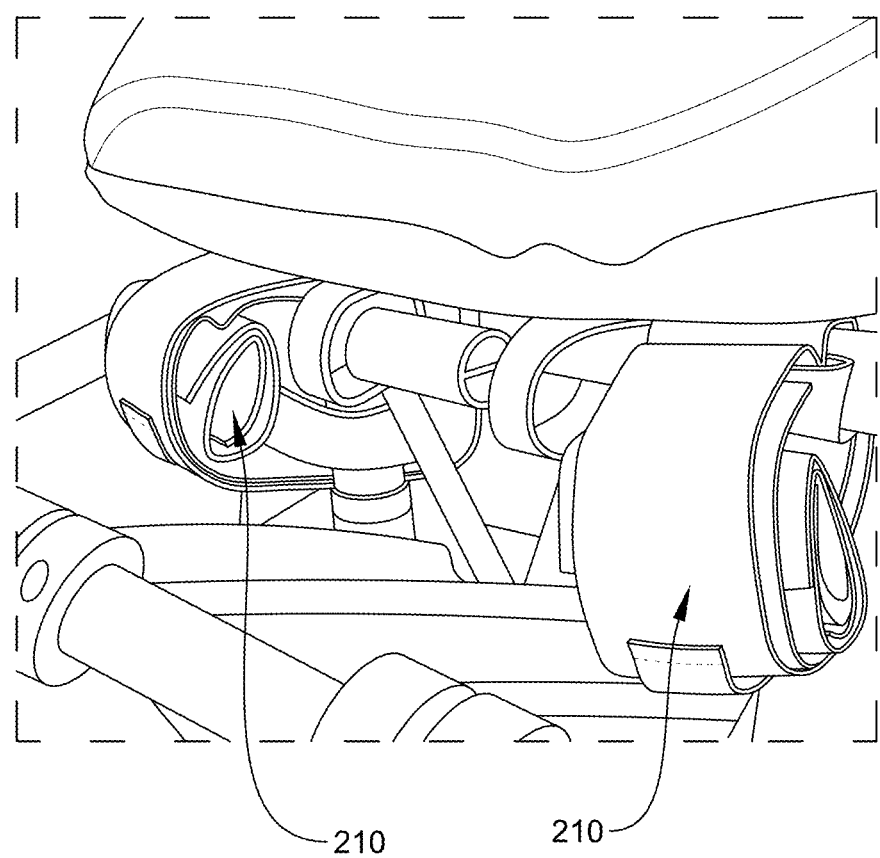
FIG. 14 is another perspective view of the foot section of the cot with two restraint assemblies mounted to frame of the deck beneath the cot mattress pad supported on the cot deck.

As best seen in FIG. 14, when the mattress is placed on the deck, the restraint systems (and hence restrain assemblies) will be located beneath the mattress but are quickly accessible to a user.

I claim:

1. A restraint system for coupling to a person support apparatus, the restraint system comprising:
   a person restraint assembly comprising:
      a tether strap;
      a restraint cuff coupled to said tether strap, said tether strap and said restraint cuff being foldable in a compact stowed configuration wherein said person restraint assembly has a restraint assembly width when said tether strap and said restraint cuff are folded in said compact stowed configuration; and
      an anchor strap for forming an anchor loop configuration to loop around and secure the restraint system to the person support apparatus at a deployment location for use therefrom; and
   a securement strap secured to said anchor strap, said tether strap secured to said anchor strap, said securement strap having a securement strap width and a free end operable to extend over said tether strap and said restraint cuff when folded in said compact stowed configuration to thereby form a single securement loop around said tether strap and said restraint cuff when folded in said compact stowed configuration wherein said securement strap is operable to anchor said tether and said restraint cuff in said compact stowed configuration to the patient support apparatus via said anchor strap and further retain said tether strap and said restraint cuff in said compact stowed configuration while said restraint system remains anchored to the patient support apparatus via said anchor strap wherein said single securement loop forms two opposed open sides when looped around said tether strap and said restraint cuff and wherein said securement width of said securement strap is less than said restraint assembly width leaving at least the tether strap visible and extended through said opposed open sides of the single securement loop, and said securement strap having a pull tab and a releasable fastener to releasably retain said tether strap and said restraint cuff in said compact stowed configuration when looped around said tether strap and said restraint cuff, wherein when said releasable fastener of said securement strap is released by pulling on said pull tab, said tether strap and said cuff may be deployed from said compact stowed configuration for use as a limb restraint while still being secured to said anchor strap.

2. The restraint system according to claim 1, wherein said tether strap is releasably coupled to said anchor strap.

3. The restraint system according to claim 1, wherein said fastener comprises a hook and loop strip at said free end of said securement strap to form said single securement loop with said securement strap around said tether strap and said cuff when in their compact stowed configuration.

4. The restraint system according to claim 3, wherein said tether strap includes an adjustment mechanism.

5. The restraint system according to claim 3, wherein said pull tab comprises a loop depending from said securement strap.

6. The restraint system according to claim 1, wherein said securement strap is releasably coupled to said anchor strap by a hook and loop strip.

7. The restrain system according to claim 1, further comprising a base, said base coupling said tether strap to said anchor strap.

8. The restraint system according to claim 7, wherein said tether strap is releasably coupled to said base.

9. The restraint system according to claim 1, further comprising a cover enclosing said tether strap and said restraint cuff when in said folded configuration, said securement strap extending around said cover.

10. The restraint system according to claim 9, wherein said cover comprises a polymer film.

11. The restraint system according to claim 1, wherein said anchor strap includes hook and loop strips for securing said anchor strap in said anchor loop configuration for securing said restraint system to the person support apparatus.

12. The restraint system according to claim 1, wherein said tether strap includes an adjustment mechanism.

13. The restraint system according to claim 12, wherein said tether strap includes an upper portion coupled to said cuff and a lower portion secured to said anchor strap, and said adjustment mechanism operable to releasably couple said upper portion to said lower portion.

14. The restraint system according to claim 13, wherein said lower portion is releasably coupled to said anchor strap.

* * * * *